United States Patent
Wei

(10) Patent No.: US 10,300,203 B2
(45) Date of Patent: May 28, 2019

(54) PRIMING MECHANISM FOR AUTOMATIC INJECTION DEVICE

(71) Applicant: Min Wei, Carmel, IN (US)

(72) Inventor: Min Wei, Carmel, IN (US)

(73) Assignee: Min Wei, Carmel, IN (US)

( * ) Notice: Subject to any disclaimer, the term of this patent is extended or adjusted under 35 U.S.C. 154(b) by 0 days.

(21) Appl. No.: 15/665,519

(22) Filed: Aug. 1, 2017

(65) Prior Publication Data

US 2018/0036488 A1 Feb. 8, 2018

Related U.S. Application Data

(60) Provisional application No. 62/370,662, filed on Aug. 3, 2016.

(51) Int. Cl.
*A61M 5/315* (2006.01)
*A61M 5/31* (2006.01)
*A61M 5/20* (2006.01)

(52) U.S. Cl.
CPC ............ *A61M 5/3146* (2013.01); *A61M 5/20* (2013.01); *A61M 5/3155* (2013.01); *A61M 5/31548* (2013.01); *A61M 5/31576* (2013.01)

(58) Field of Classification Search
CPC .. A61M 5/3146; A61M 5/20; A61M 5/31548; A61M 5/3155; A61M 5/31576
See application file for complete search history.

(56) References Cited

U.S. PATENT DOCUMENTS

| | | | | |
|---|---|---|---|---|
| 4,792,329 A | * | 12/1988 | Schreuder | A61M 5/284 604/191 |
| 8,945,050 B2 | * | 2/2015 | Wei | A61M 5/425 604/110 |
| 2010/0022963 A1 | * | 1/2010 | Edwards | A61M 5/2053 604/197 |
| 2011/0213299 A1 | * | 9/2011 | Cronenberg | A61M 5/2033 604/82 |
| 2013/0296795 A1 | * | 11/2013 | Ekman | A61M 5/2033 604/197 |

* cited by examiner

*Primary Examiner* — Edelmira Bosques
(74) *Attorney, Agent, or Firm* — Min Wei

(57) ABSTRACT

A priming mechanism for operating an automatic injection apparatus to ensure medication contents are properly delivered prior to a needled syringe of the apparatus being injected. The priming mechanism includes a push rod to move plunger(s) within the syringe; a releasable support including bendable supporting arms, which limiting motion of the syringe relative to an upper housing body before and during priming; and a recess element inside the lower housing body to release said bendable arm to allow motion of the syringe relative to the upper housing body in distal direction after priming. In one form, the priming mechanism is used for removing air bubble before injection to ensure delivering correct dose. In another form, the priming mechanism is used to mix different contents in a dual chamber syringe before injection.

6 Claims, 5 Drawing Sheets

PRIMING MECHANISM FOR AUTOMATIC INJECTION DEVICE

CROSS-REFERENCE TO RELATED APPLICATIONS

This application claims the benefit of U.S. Provisional Application Ser. No. 62/370,662, filed Aug. 3, 2016.

BACKGROUND OF THE INVENTION

The present invention pertains to pharmaceutical injection devices, and, in particular, to a priming mechanism for an automatic injection device.

Currently, biologic drugs account for more than half of all therapeutic drug candidates in pharmaceutical development pipelines. These biologic drugs need to be delivered through the parenteral route. As the parenteral therapeutic drugs become more and more popular, portable automatic medication delivery devices for self-administration are expected to be widely used together with the parenteral therapeutic drugs (also referred as combination products). One type of such device is an automatic injector device. This type of device, when triggered by a user, automatically inserts into the user a needle of a pre-filled syringe that prior to triggering was disposed within the device housing, and then automatically injects a dose of medication through that inserted needle. One difficulty with designing an automatic injector is ensuring that air bubble inside the pre-filled syringe is removed before injection (priming). This is especially true for automatic injector devices that deliver variable dose. Moreover, priming is also an essential step for using dual chamber reconstitution syringe as medication container in an automatic injector device.

International Publication Number WO 2016/036600 explains in additional details about automatic injector devices that deliver variable dose. For the variable dosing automatic injectors, it is important to remove the air bubble before injection in order to deliver correct dose. Therefore, it would be desirable to provide a priming mechanism for those automatic injection apparatus.

Besides, the priming mechanism in this invention can be utilized for automatic injector devices that carry dual chamber reconstitution syringes. Example of dual chamber reconstitution syringes can be Vetter Lyo-Ject® dual-chamber syringe or dual chamber reconstitution syringe used for leuprolide acetate injection (Lupron Depot®). To utilize automatic injector devices with reconstitution syringe, it is important to mix liquid form and dry form contents immediately prior to application.

In summary, what is needed is a new priming mechanism for utilizing automatic injector device when delivering variable dose or mixing different contents before injection.

SUMMARY OF THE INVENTION

In one form thereof, the present invention provides a priming mechanism in an automatic injection apparatus having a housing (upper and lower body), a needled syringe with one or more elastomeric plunger(s), and a plurality of biasing elements for moving the needled syringe in a first direction within the housing to extend the needle of the syringe beyond the housing, and to advance plunger(s) to force syringe contents through the needle for an injection. The priming mechanism includes a releasable support for the syringe, the releasable support including a set of bendable supporting arms that hold the syringe in place before and during priming; a lower housing body that will release the bendable arms after priming; a push rod to move elastomeric plunger(s) in the syringe during priming.

One advantage of the present invention is that a priming mechanism may be provided which can be adapted for use with differently configured automatic injector devices delivering variable dose, for example, devices presented in International Publication Number WO 2016/036600.

Another advantage of the present invention is that a priming mechanism may be provided which can be adapted for use with differently configured automatic injection devices delivering fixed dose, where the fixed dose is portion of the overall content.

Another advantage of the present invention is that a priming mechanism may be provided which can be adapted for use with differently configured automatic injection devices delivering fixed dose, where air bubble(s) need to be removed before injection.

Another advantage of the present invention is that a priming mechanism may be provided for an automatic injection device that helps to change the pre-set dose.

Another advantage of the present invention is that a priming mechanism may be provided for an automatic injection device that carries a dual chamber reconstitution syringe.

Another advantage of the present invention is that a priming mechanism may be provided for automatic injection devices that carry dual chamber syringe for mixing two different liquid contents before injection.

Still another advantage of the present invention is that a priming mechanism may be provided for an automatic injection devices in which cartridge is used as pre-filled container instead of syringe.

BRIEF DESCRIPTION OF THE DRAWINGS

The figures are schematic and simplied for clarity, and they just show details, which are essential to the understanding of the invention, while other details are left out. Throughout, the same reference numerals are used for identical or corresponding parts. Some embodiments are illustrated by way of example and not limitation in the figures of the accompanying drawings in which.

DETAILED DESCRIPTION OF THE INVENTION

Figure 1:
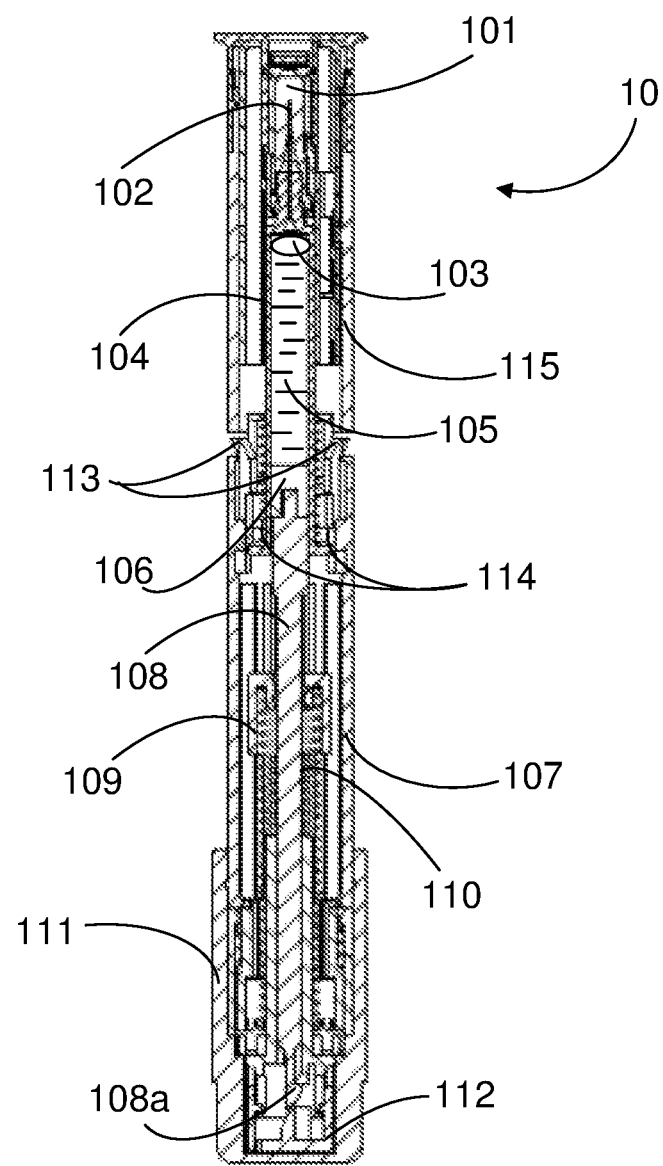
FIG. 1 shows cross-sectional view of an exemplary automatic injection device for variable dose injection, with a priming mechanism, according to the invention.

The present invention will become more fully understood from the detailed description given hereinbelow and the accompanying drawings which are given by way of illustration only, and thus, are not limitive of the present invention, and wherein:

The apparatus and methods presented herein can be used for delivering any of a variety suitable therapeutic agents or substances, such as a drug, into a patient. Initially it may be convenient to define that, the term "distal end" is meant to refer to the end of the automatic medication injector device where needle inserted into the patient, whereas the term "proximal end" is meant to refer to the end opposite to the "distal end" along the longitudinal axis of the device body. The words "upper", "lower", "right" and "left" designate directions in the drawings to which reference is made. The Words "inward" and "outward" refer to directions toward and away from, respectively.

Figure 2:
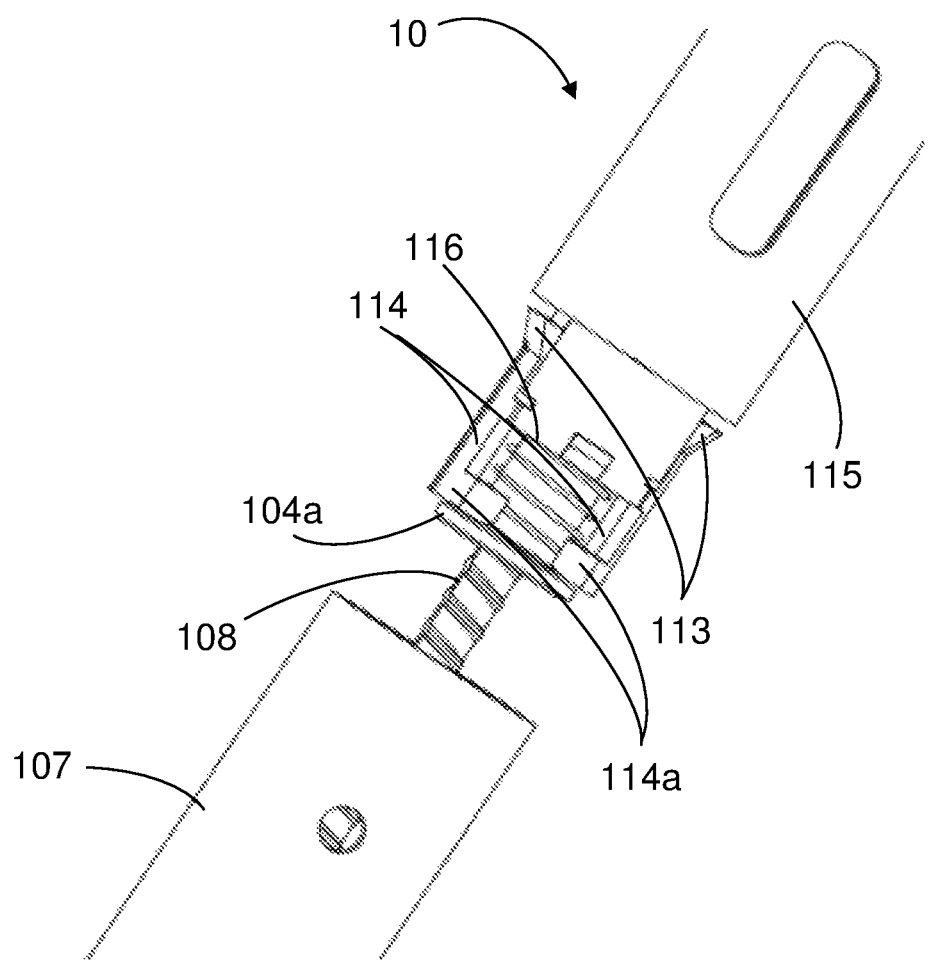
FIG. 2 is an exploded view of the exemplary automatic injection device for variable dose injection, with a priming mechanism, according to the invention.
Figure 3:
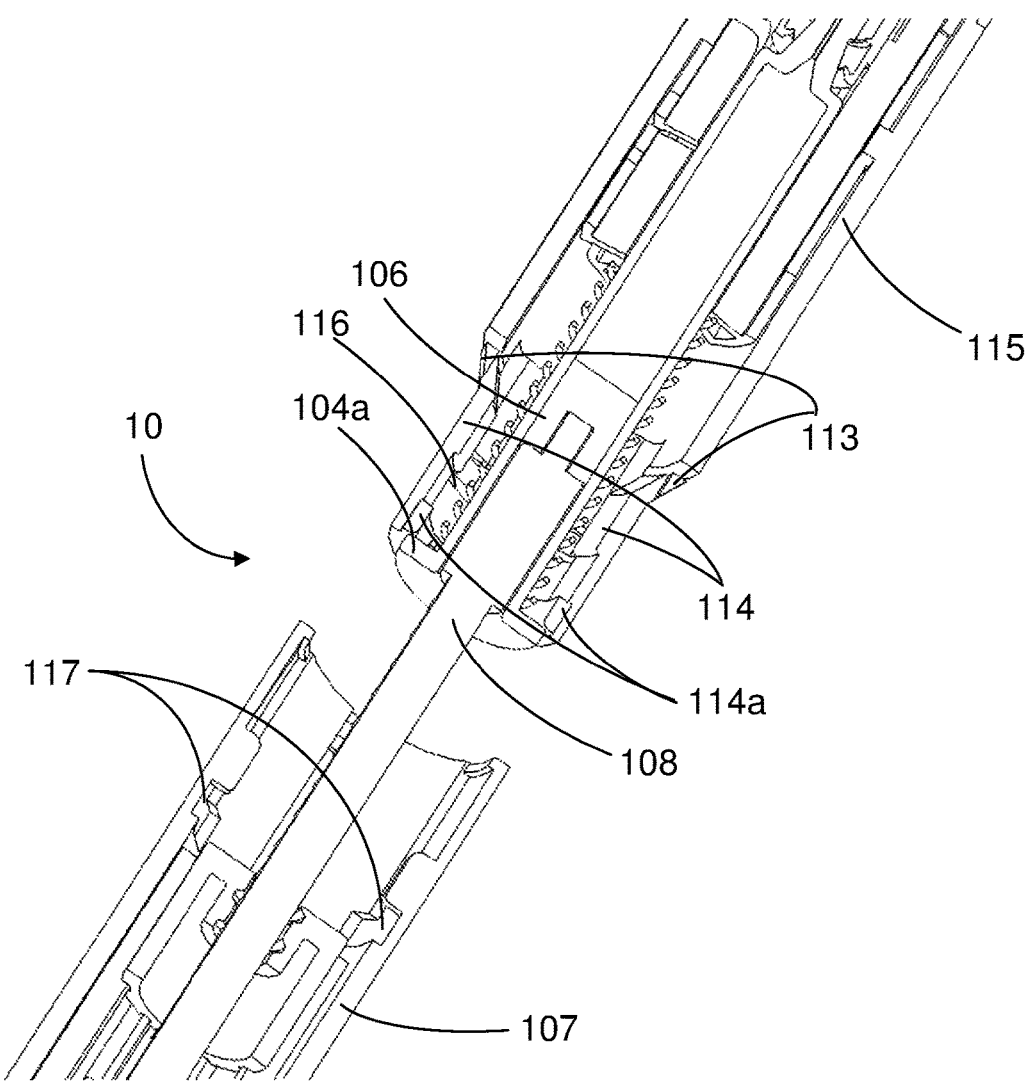
FIG. 3 is an exploded cross-sectional view of the exemplary automatic injection device for variable dose injection, with a priming mechanism, according to the invention.

FIGS. 1-3 illustrate the construction and function mechanism of an exemplary automatic injection device 10 according to the invention. With reference to FIG. 1, in this automatic injection device assembly 10, a pre-filled syringe 104, as medication container, can be made of either glass or plastic materials. The syringe 104 is of a generally standard design with an injection needle 102 mounted at its distal end which is in fluid communication with the medication contents of the syringe barrel. Liquid medication 105 and air bubble 103 inside of the pre-filled syringe 104 are sealed by a piston 106 and an elastomeric needle shield 101. The elastomeric needle shield 101 is placed at the distal end of the syringe 104. A cap 111 is used to set the injection dose. A push cap 112 is used to activate an automatic injection. Before injection, the automatic injection device assembly 10 is shown with a push rod 108 in a locked state, against biasing force of a driving spring 110, by a releasable latch mechanism formed through a hook feature 108a on the push rod 108. More detailed functional description of the automatic injection device 10 can be found in International Publication Number WO 2016/036600. The priming mechanism for the automatic injection device 10 includes a set of bendable supporting arms 114 that hold the syringe 104 in place before and during priming; an lower housing body 107 and the push rod 108. Right before priming, the needle shield 101 is removed to allow the air bubble 103 can be pushed out distally through a needle 102 during priming. With reference to FIGS. 2 and 3, during priming, an upper housing body 115 is pushed toward to the proximal end of the device 10. During this movement, supporting arms 114 keep syringe 104 stationary relative to the upper housing body 115, through stopping collar 114a supporting a flange feature 104a on the syringe 104, while the push rod 108 moving toward to the distal ends of the syringe 104 and the device 10. At the same time, the piston 106 is pushed by the push rod 108 toward to the distal end of the syringe 104. Consequently, the air bubble 103 is pushed out of the syringe 104 from the distal end of the syringe 104. At the end of priming, the lower housing body 107 restrains two prongs 113 and forces two prongs 113 to move inward. The inward movement of such prongs 113 causes two supporting arms 114 to splay outward. Once two supporting arms 114 splay outward and two stopping collar 114a reside in recessing features 117 on the lower housing body 107, the syringe 104 is freed to move distally. Then, once the push cap 112 is pushed toward to the distal end of the device 10, the releasable latch mechanism formed through hook feature 108a on the push rod 108 is released, and the driving spring 110 urges the push rod 108 move toward to the distal end of the device 10, through element 109. The driven motion of the push rod 108 shifts the syringe 104 distally relative to the upper housing body 115 and cause the tip of needle 102 to project beyond the device distal end for penetrating a user's skin. The syringe movement is stopped when the flange feature 104a lands on the stopping feature 116 on the upper housing body 115. Then, the liquid medication 105 is forced through the needle 102 for an injection.

Figure 4:
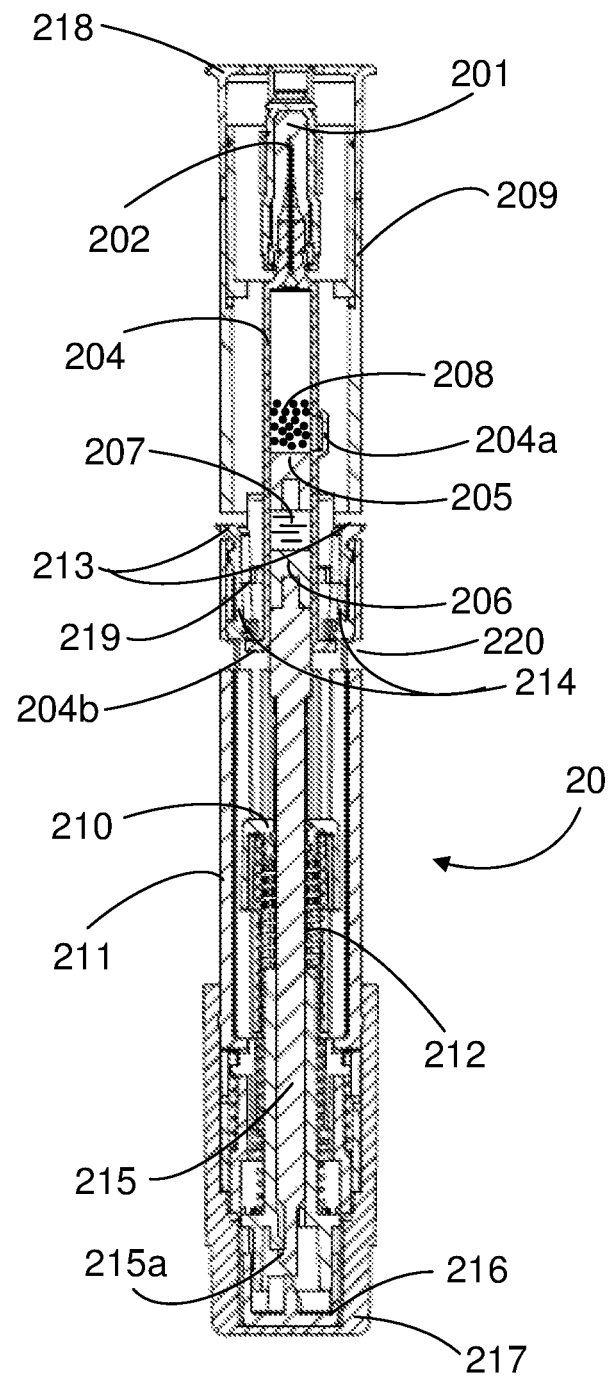
FIG. 4 shows a cross-sectional view of an exemplary automatic injection device that carries a dual chamber reconstitution syringe, with a priming mechanism, according to the invention.
Figure 5:
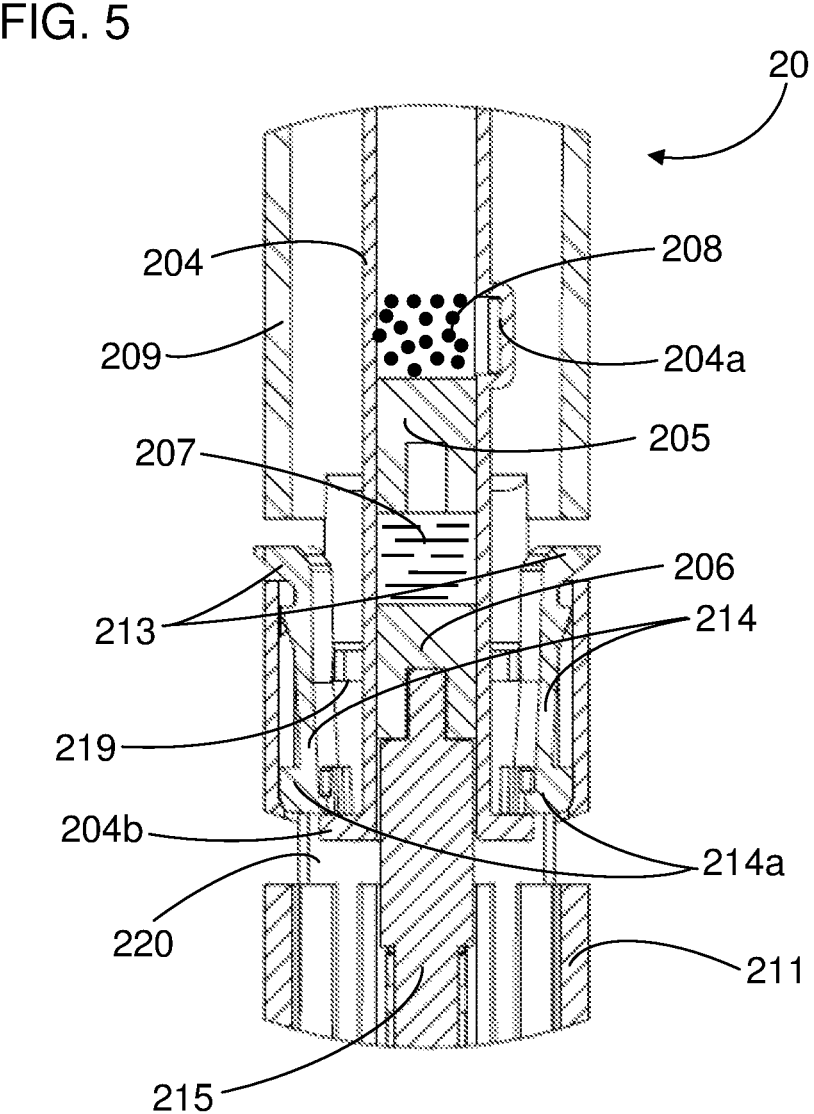
FIG. 5 shows a detailed cross-sectional view of an exemplary automatic injection device that carries a dual chamber reconstitution syringe, with a priming mechanism, according to the invention.

FIGS. 4 and 5 illustrate cross-sectional views of an exemplary automatic injection device 20 carrying a dual chamber reconstitution syringe, according to this invention. In this automatic injection device 20, a pre-filled dual chamber reconstitution syringe 204 is used as medication container. The syringe 204 has an injection needle 202 mounted at its distal end which is in fluid communication with the medication contents of the syringe barrel. The syringe 204 has a by-pass channel 204a and a flange feature 204b. Liquid content 207 is sealed by two pistons 205/206 and solid content 208 is sealed between piston 205 and an elastomeric needle shield 201. The elastomeric needle shield 201 is placed at a the distal end of the dual chamber reconstitution syringe 204. A needle shield puller 218 is used to remove the needle shield 201 before injection. A protection cap 217 is used to protect a push cap 216. The push cap 216 is used to activate an automatic injection. Before injection, the automatic injection device assembly 20 is shown with a push rod 215 in a locked state, against biasing force of a driving spring 212, by a releasable latch mechanism formed through hook feature 215a on the push rod 215. The activation mechanism of the automatic injection device 20 is the same as the automatic injection device 10. The priming mechanism for the automatic injection device 20 is to mix the liquid content 207 and solid content 208 before injection. This priming mechanism includes a set of bendable supporting arms 214 that hold the syringe 204 in place before and during priming; an lower housing body 211 and the push rod 215. During priming, an upper housing body 209 is pushed toward to the proximal end of the device 20. During this movement, the supporting arms 214 keep syringe 204 stationary relative to the lower housing body 211, through stopping collar 214a supporting a flange feature 204b on the syringe 204, while the push rod 215 moving toward to the distal ends of the syringe 204 and the device 20. At the same time, the piston 206, liquid content 207 and the piston 205 are pushed by the push rod 215 toward to the distal end of the syringe 204. When the piston 205 moves further distally and is aligned with the by-pass channel 204a, the liquid content 207 flows through the by-pass channel 204a and mix together with the solid content 208. Then, user shakes the injection device 20 to ensure the solid content 208 is dissolved or homogeneously suspended in the liquid content 207 for medication injection. At the end of priming, the lower housing body 211 restrains two prongs 213 and forces two prongs 213 to move inward. The inward movement of such prongs 213 causes two supporting arms 214 along with two stopping collar 214a to splay outward. Once two stopping collar 214a splay outward and reside in recessing features 220 on the lower housing body 211, the syringe 204 is freed to move distally. The recessing features 220 are opening slots. When the two stopping collars 214a reside in the recessing feature 220 on the lower housing body 211, it is indicated that the priming is completed. Before injection, the needle shield 218 is removed so that the medication (mixture of liquid content 207 and solid content 208) can be pushed out distally through a needle 102. Then, the protection cap 217 is removed and the push cap 216 is pushed toward to the distal end of the device 20, the releasable latch mechanism formed through hook feature 215a on the push rod 215 is released, and the driving spring 212 urges the push rod 215 move toward to the distal end of the device 20, through element 210. The driven motion of the push rod 215 shifts the syringe 204 distally relative to the upper housing body 209 and cause the tip of needle 202 to project beyond the device distal end for penetrating a user's skin. Then, the medication (mixture of liquid content 207 and solid content 208) is forced through the needle 202 for an injection.

All the features in the above embodiments and design concepts herein can be inter-changed and combined to generate new device designs. Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. In an automatic injection apparatus having an upper housing body, a lower housing body, a syringe with a piston, and a resilience member for moving said syringe in distal direction within said upper housing body, and to advance said piston to force syringe content out for an injection, a priming mechanism comprising:
   a push rod to move said piston in distal direction within said syringe to remove an air bubble within said syringe;
   a releasable support including a bendable supporting arm, said bendable supporting arm limiting motion of said syringe relative to said upper housing body in distal direction before and during priming, wherein a proximal end of said bendable supporting arm provides a stopping collar to support a flange on said syringe, and wherein a distal end of said bendable supporting arm provides a prong element extending outward; and
   a recess element inside said lower housing body to release said bendable supporting arm to allow motion of said syringe relative to said upper housing body in distal direction after priming.

2. The priming mechanism of claim 1, wherein said lower housing body restrains said prong element and causes said prong element move inward at end of priming, and wherein inward movement of said prong element causes said stopping collar to splay outward to free said syringe.

3. The priming mechanism of claim 1, wherein said recess element inside said lower housing body is an open slot providing indication for completion of priming.

4. In an automatic injection apparatus having an upper housing body, a lower housing body, a syringe with more than one chambers sealed by more than one piston and a by-pass channel, and a resilience member for moving said syringe in distal direction within said upper housing body, and to advance said piston to force syringe contents out for an injection, a priming mechanism comprising:
   a push rod to move said piston in distal direction within said syringe to mix more than one contents within said syringe;
   a releasable support including a bendable supporting arm, said bendable supporting arm limiting motion of said syringe relative to said upper housing body in distal direction before and during priming, wherein a proximal end of said bendable supporting arm provides a stopping collar to support a flange on said syringe, and wherein a distal end of said bendable supporting arm provides a prong element extending outward; and
   a recess element inside said lower housing body to release said bendable supporting arm to allow motion of said syringe relative to said upper housing body in distal direction after priming.

5. The priming mechanism of claim 4, wherein said lower housing body restrains said prong element and causes said prong element move inward at end of priming, and wherein inward movement of said prong element causes said stopping collar to splay outward.

6. The priming mechanism of claim 4, wherein said recess element inside said lower housing body is an open slot providing indication for completion of priming.

\* \* \* \* \*